United States Patent [19]

Reimer

[11] 4,134,923

[45] Jan. 16, 1979

[54] PROCESS FOR PRODUCING A METAL HYDROXIDE ADDUCT OF A TRIARYLBORANE

[75] Inventor: Ronald A. Reimer, Orange, Tex.

[73] Assignee: E. I. Du Pont de Nemours and Company, Wilmington, Del.

[21] Appl. No.: 830,043

[22] Filed: Sep. 2, 1977

[51] Int. Cl.$^2$ .............................................. C07F 5/02
[52] U.S. Cl. .............................................. 260/606.5 B
[58] Field of Search .................................. 260/606.5 B

[56] References Cited

U.S. PATENT DOCUMENTS

| | | | |
|---|---|---|---|
| 3,090,801 | 5/1963 | Washburn et al. | 260/606.5 B |
| 3,119,857 | 1/1964 | Yates et al. | 260/606.5 B |
| 3,187,054 | 1/1965 | Willcockson et al. | 260/606.5 B |
| 4,045,495 | 8/1977 | Nazarenko et al. | 260/606.5 B |
| 4,046,815 | 9/1977 | Nazarenko et al. | 260/606.5 B |

OTHER PUBLICATIONS

Fowler et al., JACS 62, 1143–1144 (1940).

*Primary Examiner*—Helen M. S. Sneed

[57] ABSTRACT

Process for producing an alkali and/or alkaline earth metal hydroxide adduct of a triarylborane from the amine adduct thereof which comprises reacting an aqueous mixture of said amine adduct with an alkali and/or alkaline earth metal hydroxide at elevated temperature, e.g., 60-130° C, removing substantially all of the amine liberated during the reaction, e.g., by stripping with an inert gas and thereby forming the metal hydroxide adduct of said borane. The process is preferably applied to the ammonia adduct of triphenylborane which adduct is generated in the treatment of a waste stream from the hydrocyanation process. Sodium is the preferred metal because the sodium hydroxide adduct is an intermediate in the production of triarylboranes which are useful as catalyst promoters.

6 Claims, 1 Drawing Figure

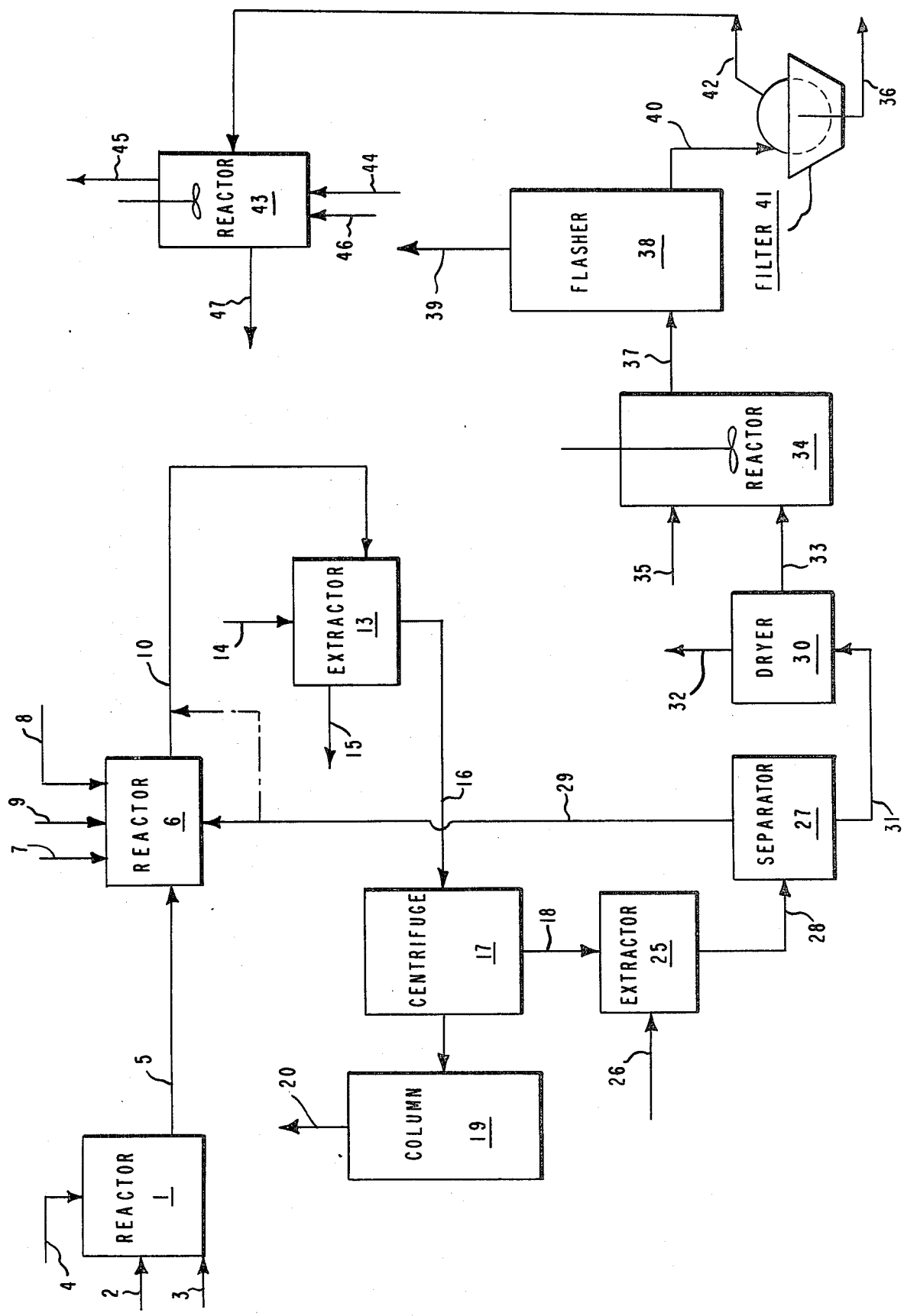

PROCESS FOR PRODUCING A METAL HYDROXIDE ADDUCT OF A TRIARYLBORANE

BACKGROUND OF THE INVENTION

Field of the Invention

The present invention relates to the recovery and reuse of catalyst components from process residue and more particularly, to a process for preparation of the hydroxide adducts of triarylboranes from the amine adducts of the boranes. The amine adduct, e.g., the ammonia adduct of triphenylborane is obtained from the treatment of the process residue from the hydrocyanation of olefins, e.g., from the preparation of adiponitrile by hydrocyanation of butadiene using nickel or palladium complexes as catalysts with triphenylborane as the catalyst promoter.

DESCRIPTION OF THE PRIOR ART

U.S. Pat. No. 3,119,857 discloses the preparation of organoboron compounds by reacting an organo-alkali metal with a boron trihalide or an ester of boric acid in an inert liquid reaction medium to produce the corresponding organo boron halide or organo boric acid ester.

Another process for the preparation of organo boron compounds is disclosed in U.S. Pat. No. 3,187,054 which method involves reacting a boron trihalide, boron ester or boron-carbon compound with an organosodium compound in an inert hydrocarbon solvent. The preparation of a variety of aryl polyboronic acids and esters by reacting an aromatic halide with finely dispersed metallic sodium in the presence of a borate ester preferably at atmospheric pressure and at temperatures below about 50° C. is disclosed in U.S. Pat. No. 3,090,801. The preparation of sodium hydroxide salt of triphenylborane by reacting triphenylborane with sodium hydroxide is disclosed by Wittig and Raff in an article entitled *Uber Komplexbildung mit Triphenyl-bor*, Ann, 573 208 (1951). The preparation of related compounds, e.g., alkyl phosphines, is disclosed in U.S. Pat. No. 3,223,736.

Some chemistry has been disclosed for the reactions involving the ammonia adduct of triarylborane. Ammonia displacement from this adduct by reacting the adduct with quaternary ammonium fluoride and hydroxide salts in the presence of ethanol to produce complex salts is disclosed by D. L. Fowler and C. A. Kraus, *J. Am. Chem. Soc.*, 62, 1143 (1940). This adduct was reacted with dry hydrochloric acid in the presence of ether by Mikhailov et al. [Izvest. Akad. Nauk S.S.S.R., Otdel. Kimm. Nauk, 812 (1957)] to produce triphenylborane and ammonium chloride. G. Wittig et al. [Ann. Chem., 573, 195 (1951)] produced triphenylborane by thermally decomposing $(CH_3)_3NH+B(C_6H_5)_4^-$ and further disclose the preparation of the sodium hydroxide salt of triphenylborane by fusion of the borane with sodium hydroxide and the reaction of the salt with ammonium chloride or hydroxide to yield $\phi_3\text{-B-NH}_3$. The borane was also reacted with sodium cyanide to yield a compound postulated to have the formula $[\phi_3(CN)B]Na$.

SUMMARY OF THE INVENTION

A process for producing an alkali and/or alkaline earth metal adduct, e.g., the sodium hydroxide adduct of triarylborane, e.g., triphenylborane from the amine adduct thereof which comprises reacting the amine adduct, e.g., as an aqueous slurry with the metal hydroxide at elevated temperature, e.g., 60–130° C., removing substantially all of amine liberated during the reaction, e.g., by stripping the solution with an inert gas such as nitrogen or steam and thereby forming the hydroxide adduct of the borane.

DETAILED DESCRIPTION OF THE PRESENT INVENTION

It has now been discovered that the hydroxide and amine adducts of the triarylboranes can exist in equilibrium as illustrated by the following equation for the ammonia adduct.

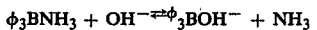

$$\phi_3BNH_3 + OH^- \rightleftharpoons \phi_3BOH^- + NH_3$$

The conversion of the ammine adduct to the hydroxide adduct is accomplished by removing the volatile amine from the medium under appropriate conditions and driving the equilibrium to the right side of the above equation to thereby substantially convert all of the amine adduct to the hydroxide adduct.

The amine adducts to which the process of the present invention can be applied include adducts with volatile amines such as pyridines; primary and secondary amines containing up to 12 carbon atoms and tertiary amines containing up to 6 carbon atoms. Volatile amines are amines which can be distilled (including azeotropic distillation) at less than 120° C., optionally under vacuum and preferably are amines which have a boiling point at atmospheric pressure of less than 120° C. Specific examples of operable amines include ammonia, mono and di methyl and ethyl amine, dodecylamine, cyclohexylamine, aniline, N-methylaniline, dihexylamine, tributylamine, N-butylamine, 2-methylpyridine, 2,4-dimethylpyridene and piperidine.

Although a wide variety of conditions can be employed to convert the amine to the hydroxide adduct, it is preferred to provide a reaction medium which does not react with, or cause degradation of the amine or the adduct. Preferably the hydroxide adduct is soluble in the medium. Examples of suitable media include but are not necessarily limited to water, alcohols containing 1–4 carbon atoms and mixtures of the foregoing of which water is the preferred medium.

The reaction temperature is not critical but elevated temperatures, e.g., 60–150° C. and preferably 60–130° C. accelerate the interchange and increase the volatility of the amine for easier removal from the system. Temperatures in excess of 130° C. can result in increased degradation of the adducts which are quite stable at lower temperatures and can require more complex equipment to handle the increased temperatures and pressures.

The pressure under which the reaction is conducted may also vary widely but is selected in view of the temperature and the amine to be removed. Pressures in the range of 3 to 40 psia are preferred.

As should be apparent to those skilled in the art in view of the above-disclosed equation, the production of the hydroxide adduct is favored by increased hydroxide concentration in the medium. However, the excess hydroxide must be neutralized before the borane can be recovered in free form, e.g., as the triarylborane and for this reason it is preferred to employ only slightly more hydroxide than is required to assure substantially complete displacement of the amine. In one embodiment of the present invention as disucssed in more detail hereinbelow, it is preferred to have the product of the present process closely match the intermediate product from the borane synthesis to which the hydroxide adduct is recycled. In this latter case, the preferred concentration of hydroxide is in the range 2.5 to 10% by weight based upon the weight of the reaction medium.

One preferred embodiment of the present process involves integration thereof with a process for the preparation of triarylboranes. The later process includes reacting a finely divided alkali metal, e.g., sodium metal, having a particle size in the range 1–100$\mu$ with an aryl halide, e.g., chlorobenzene and an orthoborate ester, e.g., those derived from secondary alkyl alcohols, e.g., isopropyl alcohol and sec-butyl alcohol in an inert organic hydrocarbon solvent which can be maintained as a liquid at reaction conditions. Optionally, promoters such as benzene to increase electron transfer and isopropyl alcohol to activate the alkali metal can be added. The reaction is conducted in the absence of significant amounts of water, i.e., under substantially anhydrous conditions. The reaction products are contacted with water to form the sodium hydroxide adduct of triarylborane. The adduct is then acidified to a pH no less than about 6 with an acid, e.g., hydrochloric acid to recover the triarylborane. The alkali metal alkoxide salt of triarylborane can be prepared in one step by simultaneous contact of the above-discussed reactants or in two steps by initially preparing the organosodium compound and subsequently reacting that material with the orthoborate ester. The preferred triarylboranes produced by the above process include those of the formula $R_3$-B wherein the R's are the same or different and are aryl or substituted aryl groups having 6 to 12 carbon atoms, e.g., phenyl, orthotolyl, paratolyl, naphthyl, methoxy paraphenyl, paraaminophenyl, biphenyl, chlorophenyl and bromophenyl. Triphenylborane and the sodium isopropoxide adduct thereof are of particular interest. Alkali metals which are operable in the process include lithium, potassium etc. with sodium being preferred. More particularly, one embodiment of the present process involves the preparation of triphenylborane by reacting finely divided sodium, i.e., particles of <100$\mu$ with chlorobenzene and isopropyl orthoborate using cyclohexane as an inert organic solvent in one or two steps under anhydrous conditions and at a temperature in the range 15–120° C., contacting the product with water to obtain an aqueous solution of the sodium hydroxide salt or adduct of triphenylborane and acidifying the salt to a pH no less than about 6 to obtain the borane while maintaining the ratio of borane to borane hydrolysis products greater than 13/1.

The above-described boranes are used as promoters in hydrocyanation processes and in a preferred embodiment are recovered in the form of an ammonia adduct. The present invention involves treatment of that ammonia adduct and other amine adducts to produce the hydroxide adduct. The sodium hydroxide adduct of triphenylborane is of particular interest because it can be returned to the above-described step in the manufacture of the borane where the borane is in the form of the sodium hydroxide adduct.

In one embodiment of the present invention, the ammonia adduct is recovered from a waste stream from a process which involves the direct addition of 2 molecules of hydrogen cyanide to a molecule of butadiene thereby producing adiponitrile. A general disclosure of typical processes is found in the publication entitled "Hexamethylene Diamine" in The Process Economics Program Report No. 31-A, Stanford Research Institute, Menlo Park, C.A.; September, 1972. More particularly, the hydrocyanation process is disclosed in U.S. Pat. Nos. 3,496,215 issued on Feb. 17, 1970, 3,496,218 issued on Nov. 24, 1970, 3,542,847 issued on Nov. 24, 1970, and 3,752,839 issued on Aug. 14, 1973. The residue from the above-disclosed process is obtained by removing the substantial portion of desired products, unreacted materials and intermediates from the reactor effluent, separating solvent and other volatiles from the resultant stream for recycle to the reactor and thereafter obtaining a concentrated waste stream as discussed in more detail hereinbelow. The process is conducted in two steps. With reference to the drawing, the first step (reactor 1) involves the addition of one molecule of hydrogen cyanide (stream 2) to dry butadiene (stream 3) in the presence of a catalyst (stream 4) consisting of zerovalent nickel usually in the form of a nickel tetrakistritolylphosphite, to produce a mixture of cis- and trans-3-pentenenitrile and 4-pentenenitrile. This reaction mixture is withdrawn from reactor 1 via line 5, treated to remove impurities and then introduced into reactor 6 along with additional HCN (line 7), ligand (line 8) and triarylborane catalyst promoter such as triphenylborane (line 9). In this reaction which can be conducted in one or more steps, 4-pentenenitrile is formed by the in situ isomerization of 3-pentenenitrile. The 4-pentenenitrile is then converted to adiponitrile by the addition of one molecule of HCN. The effluent from the reactor 6 is passed to extractor 13 and there contacted with cyclohexane (line 14). The cyclohexane extractant (line 15) is subsequently directed to further treatment for product recovery. During the hydrocyanation as described as hereinabove a portion of the zero-valent nickel catalyst is oxidized to nickel cyanide which is insoluble in the reaction medium and which forms insoluble complexes with the triarylborane. The tails from the extraction vessel (line 16) contain such complexes which are subsequently separated from the tails (line 16) by centrifuge 17. A typical composition range of this sludge is set forth below in Table I.

TABLE I

| SLURRY COMPOSITION (% by weight) | |
| --- | --- |
| Triphenylborane ($O_3B$) | 10–70 |
| $Ni(CN)_2$ | 13–60 |
| Adiponitrile (ADN) | 10–60 |
| Methylglutaronitrile (MGN) | 1–3 |
| Pentenenitriles (PN) | 2–4 |
| Cyclohexane | 2–4 |
| (Balance - Miscellaneous Organics) | |

The liquid discharge from centrifuge 17 is distilled in column 19 to recover residual 3-pentenenitrile, cyclohexane and other volatiles overhead (line 20). Stream 18 is passed to extractor 25 where it is thoroughly contacted with mono-olefinically unsaturated nitrile introduced via line 26. The solvent is advantageously 3-pentenenitrile and in practical application is found as a recycle stream in the hydrocyanation process and particularly a stream from the treatment of stream 5.

Two typical streams which can be employed as extractants (line 26) contain the following compounds in the amounts indicated in Table II. Abbreviations following the name compounds are used in the following portion of the specification.

TABLE II

| Compound | Concentration (% by weight) | |
|---|---|---|
| | Stream A | Stream B |
| Cis-2-pentenenitrile (C2PN) | 0 | 2.0 |
| Cis-2-methyl-2-butene-nitrile (C2M2BN) | 2.0 | 9.0 |
| Valeronitrile (VN) | 0 | 3.0 |
| Trans-2-pentenenitrile (T2PN) | 0.5 | 5.0 |
| Trans-3-pentenenitrile (T3PN) | 88.0 | 55.0 |
| 4-pentenenitrile (4PN) | 2.0 | 3.0 |
| Cis-3-pentenenitrile (C3PN) | 3.0 | 10.0 |
| Ethyl succinonitrile (ESN) | .2 | 1.5 |
| 2-methylglutaronitrile (MGN) | 0.5 | 3.0 |
| adiponitrile (ADN) | 0.2 | 5.0 |

Balance - Miscellaneous Organics

After thorough contact of the extractant (line 26) with the sludge (line 18), the resultant mixture is directed to a suitable separator 27 via line 28. The liquid from separator 27 (line 29) is returned to the product recovery portion of the hydrocyanation process or to the hydrocyanation step. The treated solids can now be directed to dryer 30 via line 31 since the tar-forming organics have been extracted and replaced with more volatile nitriles which are readily removed without excessive degradation. Volatile materials which are driven from the solids during drying (line 32) can be condensed and combined with the solution in line 29. A typical analysis of the solution (line 29) and the volatile material from dryer 30 (line 32) is set forth below in Table III.

TABLE III

| Compound | Concentration (% by weight) | |
|---|---|---|
| | Stream 29 | Stream 32 |
| C-2-PN | 0.2 | 0 |
| C2M2BN | 2.5 | 1.2 |
| VN | 0.2 | 0 |
| T2PN | 0.2 | 0.4 |
| T3PN | 80.0 | 82.0 |
| 4PN | 1.5 | 1.5 |
| C3PN | 2.6 | 3.3 |
| ESN | 0.2 | 0.2 |
| MGN | 2.2 | 2.1 |
| ADN | 10.0 | 1.8 |

An analyses of the solids (line 33) is set forth below:

| Compound | Concentration (% by weight) | |
|---|---|---|
| | Range | Typical |
| Carbon | 60-75 | 61 |
| Hydrogen | 4-6 | 5 |
| Nitrogen | 8-15 | 12.5 |
| Nickel | 7-15 | 9 |
| Boron | 1-3 | 1.85 |
| Triphenylborane | | 35.2 |

The relative amounts of nickel and boron can vary from minor amounts of triphenylborane to about two moles of the borane per mole of nickel.

The solids (line 33) are transferred to pressure reactor 34 where they are contacted with an aqueous solution of a nitrogen-containing base e.g., a concentrated aqueous solution of ammonium hydroxide, introduced via line 35 in an amount sufficient to dissolve the solids, to form the soluble nickel compounds, e.g., nickel cyanide ammine and to permit the formation and subsequent precipitation of the amine adduct of triphenylborane. As will be discussed in more detail hereinbelow the concentration of base in combination with the temperature (preferably 90°-105° C.) must be high enough to prevent precipitation of the soluble nickel complex (nickel hexammine tetracyanonickelate) as insoluble nickel (II) cyanide monoammine. The liquid (line 37) from reactor 34 is conveniently passed to flasher 38 where ammonia and water are removed via line 39 which reduces the temperature and hence pressure to that of the filter 41. The soluble nickel complex (line 36) is removed from the cooled slurry (line 40) in filter 41. The filtrate (line 36) is treated to recover ammonia and precipitate the nickel (II) cyanide monoammine $[Ni(CN)_2(NH_3) \times H_2O]$. Nickel compounds can be recovered from the solids by several methods, e.g., thermal treatment.

The solids (line 42) which comprise the amine adduct of the triarylborane are treated according to the process of the present invention. The solids (line 42) are directed to stirred reactor 43 where they are thoroughly contacted with an aqueous solution of sodium hydroxide (2.5%), introduced via line 44, at elevated temperature until the shift to the hydroxide adduct is complete. The volatile amine is removed for recovery via line 45 optionally with the assistance of an inert gas or steam introduced via line 46. A solution of the hydroxide adduct is removed from reactor 43 via line 47 and can be recycled to the step in the process for the preparation of the triarylborane where the borane is in the same adduct or salt form.

Digestion of the catalyst solids and/or formation of the amine adduct of the borane (reactor 34) is not instantaneous and is accelerated with increasing temperature. Generally, reaction time of 0.5-4 hours is satisfactory. Although elevated temperatures decrease the time required for digestion and precipitation, the rate of borane degradation, i.e., the loss to undesired products, is also increased as is the complexity and cost of equipment to accommodate the pressures required to maintain the reactants in the liquid phase. For convenience of operation, it is desirable to conduct the digestion/precipitation portion of the present process at a temperature in the range 60°-150° C. and preferably at a temperature in the range 90°-120° C.

It is preferred to obtain the hydroxide adduct (line 47) substantially free of impurities especially catalyst residue, e.g., nickel compounds. Unless an excess of amine is present in the initial digestion, (reactor 34), the digestion can be incomplete and/or the nickel compounds can precipitate along with the amine adduct of the borane. This results in inefficient separation of the nickel and borane. Excess amine means amine in excess of the theoretical requirements for reaction, e.g., in the case where ammonia is the amine and the borane is triphenylborane, 4 moles of ammonia per mole of boron plus nickel are theoretically required (3 moles/mole of nickel; 1 mole/mole of boron). At nickel concentrations greater than 1% by weight based upon the weight of the solution at least 6.0% by weight ammonia should be present to assure satisfactory digestion and to maintain the nickel species in solution at temperatures below about 80° C. The nickel species are more soluble at temperatures above 80° C. and therefore less ammonia can be employed to realize satisfactory digestion and to maintain the nickel in solution. However, it is desirable to employ at least the minimum amounts above stated. Preferably, the molar ratio of ammonia to nickel plus boron is initially maintained at at least 10/1 and more preferably 15-50/1 is employed. It is also preferred to maintain the concentration of ammonia in the aqueous solution in the range 15-25%.

The foregoing discussion is directed to the use of sodium hydroxide as the hydroxide source. However, as will be readily understood by one skilled in the art any alkali or alkaline earth hydroxide which exhibits satisfactory solubility, i.e., the ability to produce sufficient hydroxide ion can be employed in the present process. Examples of such hydroxide ion sources include potassium hydroxide and calcium hydroxide.

The following examples are presented to illustrate but not to restrict the present invention. Parts and percentages are by weight unless otherwise noted.

EXAMPLE 1

Approximately 3.0 grams of the ammonia adduct of triarylborane having the formula $(C_6H_5)_3B.NH_3$ was introduced into a 250 ml round bottom flask fitted with a reflux condenser and a tube for the introduction of gas below the liquid level in the flask along with 6.0 grams of sodium hydroxide and 50 milliliters of water. The resultant mixture was heated at reflux (100° C.) for a period of five hours while passing nitrogen through the sparger at the rate of approximately 10-20 cc per minute. Substantially complete solution of ammonia adduct was realized in approximately 30 minutes from the beginning of heating and the presence of ammonia gas was detected in the purge. Through the aforementioned period a clear solution of the hydroxide adduct of triphenylborane was obtained. Approximately 32 ml of 6 M hydrochloric acid were then added to the resultant solution to titrate the solution to a pH of about 7.0 during which time a white precipitate of triphenylborane was collected in the bottom of the flask. The precipitate was recovered by vacuum filtration, washed with 10 milliliters of water at room temperature and then dried under 500 millimeters of mercury vacuum at 60° C. for a period of 30 minutes. Approximately 2.33 grams of dry solid were recovered which by analysis contained 95% triphenylborane for an overall recovery based upon the boron in the initial ammonia adduct of 78.6%.

EXAMPLE 2

A reaction flask was charged with (p-$CH_3C_6H_4)_3B.NH_3$ (5.45 g, 0.0181 mole) and 150 ml 2.5% NaOH solution (0.0938 mole NaOH). The slurry was boiled at 100° C., with occasional $H_2O$ addition to maintain volume, until wet litmus paper indicated that $NH_3$ was no longer being removed in the off-gas. Kjeldahl analysis of the reaction mixture indicated ~90% removal of $NH_3$. The resulting solution was filtered and titrated to pH of 8.3 with HCl whereupon a solid precipitate formed. The solids were submitted for infrared and elemental analysis. The infrared spectrum was similar to that of a known sample of (p-$CH_3C_6H_4)_3B$. The elemental analysis and calculated composition are shown below.

|  | % C | H | N | B |
|---|---|---|---|---|
| Analyzed | 84.3 | 7.21 | 0.09 | 3.87 |
| Calculated | 88.8 | 7.4 | — | 3.8 |

EXAMPLE 3

A reaction flask was charged with $\phi_3B.NH_2CH_3$ (1.98 g, 0.00726 mole) and 80 ml 2.5% NaOH solution (0.05 mole NaOH). Heating was carried out as in Example 2 until wet litmus paper no longer indicated the presence of monomethyl amine in the off-gas. Kjeldahl analysis of the product showed 98% removal of amine. Liquid chromatography indicated 0.00714 moles $\phi_3B$ in the product.

EXAMPLE 4

Approximately 8.0 grams of $(C_6H_5)_2(C_6H_4)$ (p-$C_6H_5$)$B.NH_3$ was charged to 60 ml of a 5% solution of sodium hydroxide which had been heated to reflux at atmospheric pressure. The ammonia adduct dissolved and after maintaining the solution at reflux with a nitrogen sparge for a period of two hours to remove ammonia, the solution was cooled and then neutralized to a pH of 9.1 in a dry box. The crystals of the free borane were recovered by filtration, washed with water and then vacuum dried at 50 mm Hg at 60° C. with a nitrogen purge. The solids were analyzed to contain 3.40% boron (calculated value 3.39%).

I claim:

1. A process for producing a metal hydroxide adduct of a triarylborane from the amine adduct thereof which comprises reacting at a temperature in the range 60°-150° C. a mixture of said amine adduct with a metal hyroxide selected from the class consisting of alkaline alkali earth and mixtures thereof, removing substantially all of amine liberated during the reaction and thereby forming the metal hydroxide adduct of said borane.

2. The process of claim 1 wherein the amine is ammonia and is removed from the mixture by stripping with an inert gas during the reaction.

3. The process of claim 1 wherein the amine is present in a reaction medium.

4. The process of claim 3 wherein the reaction medium is water.

5. The process of claim 2 wherein the amine is present in a reaction medium.

6. The process of claim 5 wherein the reaction medium is water.

* * * * *